(12) United States Patent
Choe et al.

(10) Patent No.: US 10,301,327 B2
(45) Date of Patent: May 28, 2019

(54) PREPARATION METHOD OF ANIONIC POLYMERIZATION INITIATOR, DEVICE FOR MANUFACTURING ANIONIC POLYMERIZATION INITIATOR AND ANIONIC POLYMERIZATION INITIATOR PREPARED THEREFROM

(71) Applicant: LG Chem, Ltd., Seoul (KR)

(72) Inventors: Jae Hoon Choe, Daejeon (KR); Dong Cheol Choe, Daejeon (KR); Hyun Ju Kim, Daejeon (KR); Hyeon Hui Kim, Daejeon (KR); Jong Young Choi, Daejeon (KR); Jung Yong Lee, Daejeon (KR); Woong Chan Jeong, Daejeon (KR); Jong Min Shin, Daejeon (KR); Chan Joong Kim, Daejeon (KR); Kwang Ho Song, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/577,974

(22) PCT Filed: Jul. 27, 2016

(86) PCT No.: PCT/KR2016/008193
§ 371 (c)(1),
(2) Date: Nov. 29, 2017

(87) PCT Pub. No.: WO2017/047924
PCT Pub. Date: Mar. 23, 2017

(65) Prior Publication Data
US 2018/0291038 A1    Oct. 11, 2018

(30) Foreign Application Priority Data

Sep. 17, 2015  (KR) ........................ 10-2015-0131451
Apr. 1, 2016   (KR) ........................ 10-2016-0040064
Apr. 1, 2016   (KR) ........................ 10-2016-0040066

(51) Int. Cl.
| | |
|---|---|
| B60C 1/00 | (2006.01) |
| C07F 1/02 | (2006.01) |
| C08F 2/04 | (2006.01) |
| C08F 2/44 | (2006.01) |
| C08F 2/50 | (2006.01) |
| C08F 12/08 | (2006.01) |
| C07C 211/04 | (2006.01) |
| C07D 211/80 | (2006.01) |
| C08F 212/08 | (2006.01) |
| C08F 236/06 | (2006.01) |

(52) U.S. Cl.
CPC ................ *C07F 1/02* (2013.01); *B60C 1/00* (2013.01); *C07C 211/04* (2013.01); *C07D 211/80* (2013.01); *C08F 2/04* (2013.01); *C08F 2/44* (2013.01); *C08F 2/50* (2013.01); *C08F 12/08* (2013.01); *C08F 212/08* (2013.01); *C08F 236/06* (2013.01); *B60C 1/0016* (2013.01)

(58) Field of Classification Search
None
See application file for complete search history.

(56) References Cited

U.S. PATENT DOCUMENTS

| | | |
|---|---|---|
| 5,491,230 A | 2/1996 | Lawson et al. |
| 5,502,131 A | 3/1996 | Antkowiak et al. |
| 5,554,696 A | 9/1996 | Fayt et al. |
| 5,567,815 A | 10/1996 | Hall et al. |
| 2002/0173607 A1 | 11/2002 | Brockmann |
| 2012/0101212 A1 | 4/2012 | Yoon et al. |
| 2014/0213721 A1 | 7/2014 | Yamada et al. |
| 2016/0159956 A1 | 6/2016 | Thiele et al. |

FOREIGN PATENT DOCUMENTS

| | | |
|---|---|---|
| JP | S4825745 A | 4/1973 |
| JP | S52995 A | 1/1977 |
| JP | H06056910 A | 3/1994 |
| JP | H07196713 A | 8/1995 |
| JP | H08048708 A | 2/1996 |
| JP | H08277306 A | 10/1996 |
| JP | 2013082843 A | 5/2013 |
| JP | 2014177538 A | 9/2014 |
| JP | 2015131873 A | 7/2015 |
| KR | 100658361 B1 | 12/2006 |
| KR | 20110052523 A | 5/2011 |
| KR | 20120139014 A | 12/2012 |
| KR | 20140028132 A | 3/2014 |
| RU | 2264414 C1 | 11/2005 |
| WO | 2010035990 A2 | 4/2010 |

(Continued)

OTHER PUBLICATIONS

Search report from International Application No. PCT/KR2016/008193, dated Oct. 20, 2016.

(Continued)

*Primary Examiner* — Zinna Northington Davis
(74) *Attorney, Agent, or Firm* — Lerner, David, Littenberg, Krumholz & Mentlik, LLP

(57) ABSTRACT

A method for preparing an anionic polymerization initiator, a device for manufacturing the same, and an anionic polymerization initiator prepared therefrom is provided. And the method for preparing an anionic polymerization initiator according to the present invention is characterized in that in a continuous reactor an amine compound of Formula 1 and/or Formula 2; an organometallic compound; and/or a conjugated diene compound are introduced in the form of a solution and reacted.

10 Claims, 2 Drawing Sheets

(56) References Cited

FOREIGN PATENT DOCUMENTS

WO  2013035589 A1  3/2013
WO  2015010710 A1  1/2015

OTHER PUBLICATIONS

Hirotsugu Usutani et al., "Generation and Reactions of o-Bromophenyl-lithium without Benzyne Formation Using a Microreactor", Journal of the American Chemical Society, Feb. 27, 2007, vol. 129, No. 11, pp. 3046-3047, XP055498746.
Partial Supplementary European Search Report including Written Opinion for Application No. EP16846744.7 dated August 21, 2018.
International Search Report From PCT/KR2016/008191 dated Jan. 5, 2017.
Hubert P, Soum A, Fontanille M. Structure and reactivity of propagating species in anionic polymerization of 2-vinylpyridine initiated by lithium derivatives in toluene. Macromolecular Chemistry and Physics. Apr. 1995;196(4):1023-30.
Soum AH, Tien CF, Hogen-Esch TE, D'Accorso NB, Fontanille M. Stereoregular anionic polymerization of 2-isopropenylpyridine. Die Makromolekulare Chemie, Rapid Communications. Apr. 1983;4(4):243-8.

[Figure 1]
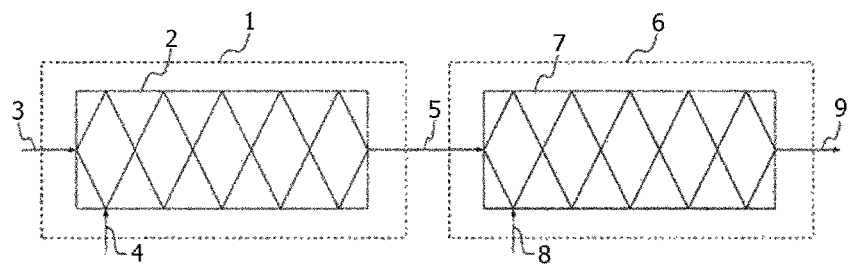
[Figure 2]
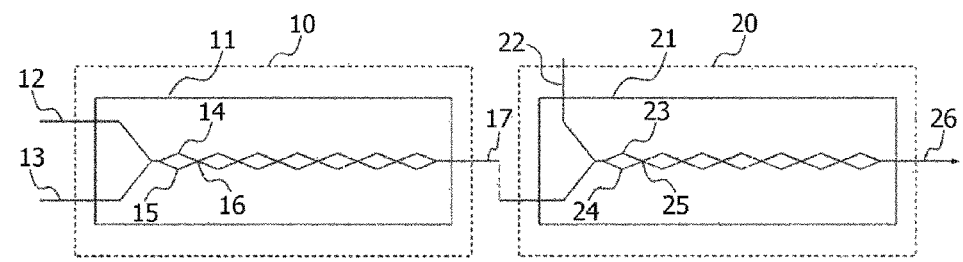
[Figure 3]
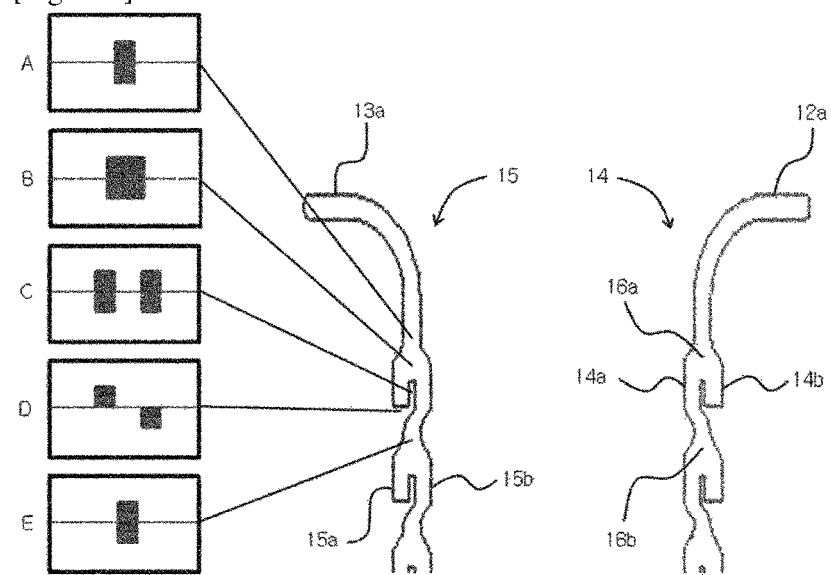

[Figure 4]
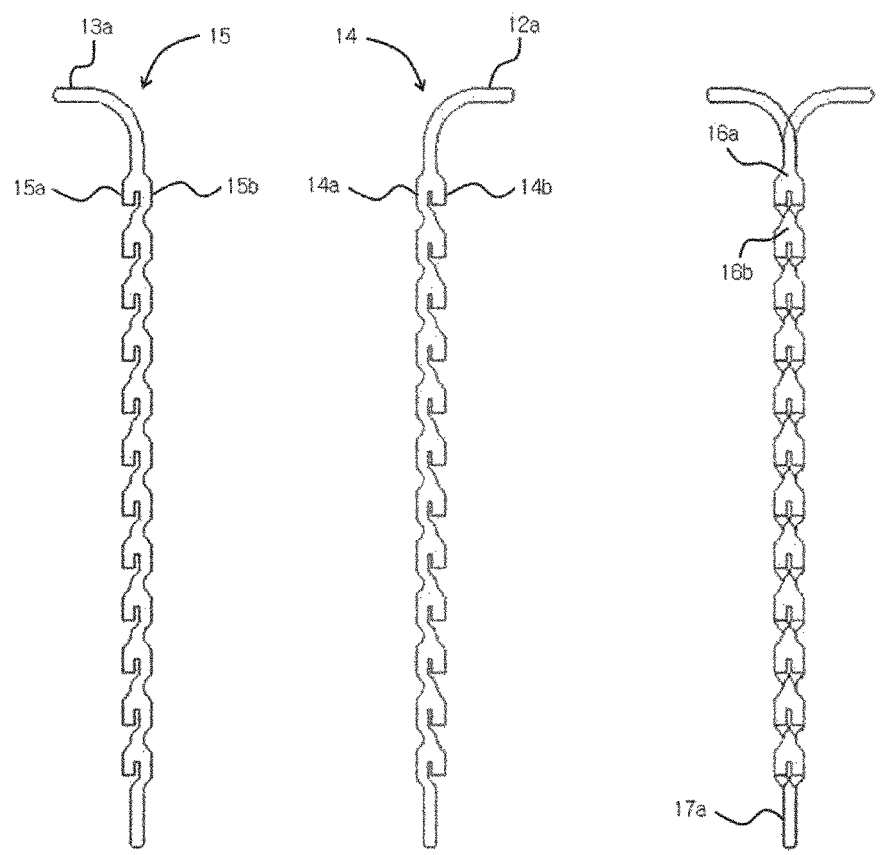
[Figure 5]
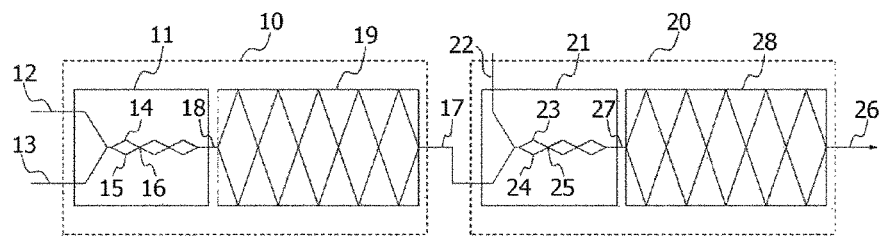

PREPARATION METHOD OF ANIONIC POLYMERIZATION INITIATOR, DEVICE FOR MANUFACTURING ANIONIC POLYMERIZATION INITIATOR AND ANIONIC POLYMERIZATION INITIATOR PREPARED THEREFROM

CROSS-REFERENCE TO RELATED APPLICATIONS

The present application is a national phase entry under 35 U.S.C. § 371 of International Application No. PCT/KR2016/008193 filed Jul. 27, 2016, which claims priority from Korean Patent Application No. 10-2015-0131451 filed Sep. 17, 2015, Korean Patent Application No. 10-2016-0040064 filed Apr. 1, 2016, and Korean Patent Application No. 10-2016-0040066 filed Apr. 1, 2016, all of which are incorporated herein by reference.

TECHNICAL FIELD

The present application relates to a method for preparing an anionic polymerization initiator, a device for manufacturing the same, and an anionic polymerization initiator prepared therefrom.

BACKGROUND ART

As physical properties of high-efficiency, environment-friendly and high-performance tires are required for reducing discharge of carbon dioxide and improving fuel economy, and the like, tire materials that meet such needs are actively being developed. Particularly, styrene-butadiene rubber obtained by solution polymerization (hereinafter, referred to as SSBR), unlike emulsion polymerization, is easy to change structure, and reduces movement of chain ends by bonding or modifying the chain ends and increases bonding force with carbon black, so that it has been used as a rubber material for tire treads. In addition, as silica filling materials are developed, low rolling resistance and high road surface braking force can be obtained at the same time, but to this end, a technique of combining hydrophilic silica with the SSBR having hydrophobicity and dispensing them therein is needed.

Such a method includes a method of surrounding silica particles themselves with a hydrophobic substance, a method of using a coupling agent between the silica and the SSBR, and the like. Recently, techniques for introducing a moiety capable of reacting and bonding with silica or a moiety for serving to assist this into the SSBR polymer chains themselves by using a modification initiator, a modifying monomer or a modifying agent, and the like upon SSBR anionic polymerization have been developed. In particular, the modification initiator is used as an essential material for preparing such a modified SSBR by initiating anionic polymerization and serving to introduce a functional group into one end of the chain.

Among anionic polymerization initiators used upon synthesizing such an SSBR, hexamethylene lithium (HMI-Li) initiator is prepared by reaction of hexamethyleneimine (HMI) and n-butyllithium (BuLi, NBL) as in the following reaction scheme.

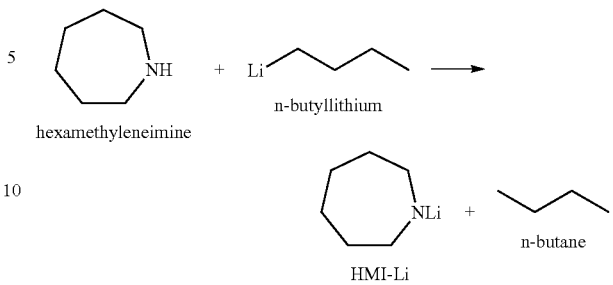

[Reaction Scheme 1]

However, HMI-Li has a low solubility in a solvent to fall into precipitation over time and also has a problem that the reactivity is lower than that of BuLi, although it can be used as an initiator. In order to solve this disadvantage, conventionally, the polymerization initiator was prepared by further reacting a conjugated diene (R) such as isoprene (IP) or 1,3-butadiene (BD) after being subjected to Reaction Scheme 1, as in the following Reaction Scheme 2. The initiator may increase the solubility in an organic solvent by further attaching such conjugated dienes to perform a stable reaction, and also has the reactivity higher than that of HMI-Li as an initiator, which is sufficient to initiate anionic polymerization.

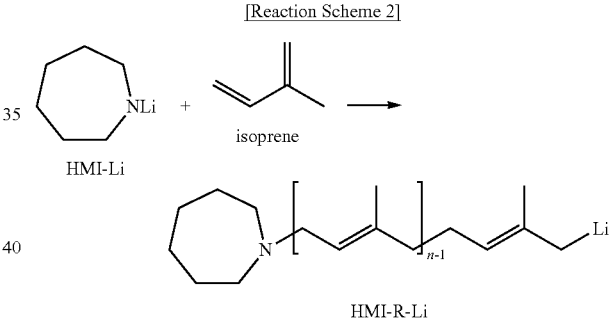

[Reaction Scheme 2]

In Reaction Scheme 2, n is an integer from 1 to 100.

However, the modification initiator thus prepared is unstable over time and falls into precipitation, or is inactivated by bonding a very small amount of oxygen with water. Therefore, the existing process of preparing the above polymerization initiator in a batch-wise manner and then introducing it into the polymerization reaction necessarily requires a storage step of the modification initiator, thereby bringing about the aforementioned disadvantages. This may adversely affect the post-processes to be a factor for lowering physical properties of the finally synthesized SSBR, which makes it difficult to maintain a constant quality.

In the prior art, an anionic polymerization initiator was prepared by a batch-wise process and then used to prepare a solution-polymerized SSBR. Or the preparation of an anionic polymerization initiator and a solution-polymerized styrene-butadiene rubber in a batch-wise reactor was carried out simultaneously in one pot.

In the case of the former, the storage step of the modification initiator is necessarily required, and during the period of storing the already synthesized initiator its anions are reacted with various scavengers such as moisture and air and thus the initiator loses its activity. This may adversely affect the post-processes to be a factor for lowering the physical properties of the finally synthesized SSBR, which makes it difficult to maintain a constant quality. In the case of the latter, it is a process of performing the polymerization reaction in the same batch-wise reactor simultaneously with the initiator synthesis reaction, whereby the problem of storage could be solved. However, it is difficult to confirm whether the modification initiator is properly synthesized, and the physical properties are also deteriorated more than the case of adding the synthesized initiator. In addition, in all the conventional batch-wise processes, by-products are produced while raw materials are directly introduced, mixed and reacted, or reverse reactions occur to generate unreacted products, and as a result, there is also a problem that a polymerization yield is lowered.

DISCLOSURE

Technical Problem

The present invention is for solving the above-described problems, and it is an object of the present invention to provide a device for manufacturing an anionic polymerization initiator capable of preventing instability and inactivation of the polymerization initiator and deterioration of physical properties of SSBR due to no need of the storage step, minimizing by-products and unreacted products and epochally improving a conversion rate, and a method for preparing an anionic polymerization initiator and an anionic polymerization initiator prepared therefrom.

Technical Solution

In order to achieve the above-described object, there is provided a method for preparing an anionic polymerization initiator comprising a step of introducing at least one amine compound selected from compounds of Formulas 1 and 2 below and an organometallic compound into a continuous reactor and reacting them:

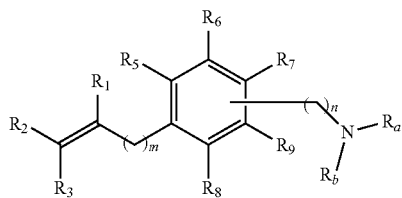

[Formula 1]

In Formula 1 above,
$R_1$, $R_2$, $R_3$, $R_5$, $R_6$, $R_7$, $R_8$ and $R_9$ independently represent hydrogen or an alkyl group having 1 to 6 carbon atoms,
$R_a$ and $R_b$ independently represent hydrogen or an alkyl group having 1 to 5 carbon atoms, and
n and m are each an integer of 0 to 20,

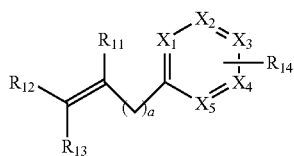

[Formula 2]

In Formula 2 above,
$R_{11}$, $R_{12}$, $R_{13}$ and $R_{14}$ independently represent hydrogen, an alkyl group having 1 to 6 carbon atoms, an alkenyl group having 1 to 6 carbon atoms or an alkynyl group having 1 to 6 carbon atoms,
$X_1$, $X_2$, $X_3$, $X_4$ and $X_5$ independently represent nitrogen or carbon, provided that at least one is nitrogen, and
a is an integer of 0 to 20.

In addition, the present invention provides a device for manufacturing an anionic polymerization initiator characterized in that the device comprises:
a mixer; and
a first inflow line and a second inflow line connected to the mixer, and
the first inflow line supplies at least one amine compound selected from the compounds of Formulas 1 and 2 according to claim 1, and the second inflow line supplies an organometallic compound.

Furthermore, the present invention provides
an anionic polymerization initiator selected from compounds of Formulas 9 and 10 below:

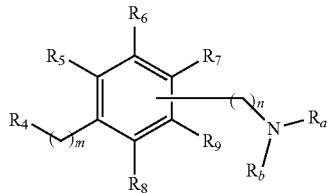

[Formula 9]

In Formula 9 above,
$R_4$ represents an alkyl lithium having 1 to 20 carbon atoms, an alkyl sodium having 1 to 20 carbon atoms, an alkyl potassium having 1 to 20 carbon atoms, an alkyl magnesium bromide having 1 to 6 carbon atoms or an alkyl magnesium chloride having 1 to 6 carbon atoms,
$R_5$, $R_6$, $R_7$, $R_8$ and $R_9$ each represent hydrogen or an alkyl group having 1 to 6 carbon atoms,
$R_a$ and $R_b$ independently represent hydrogen or an alkyl group having 1 to 5 carbon atoms, and
m and n are each an integer of 0 to 20;

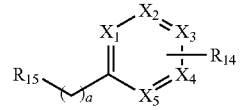

[Formula 10]

In Formula 10 above,
$R_{14}$ represents hydrogen or an alkyl group having 1 to 6 carbon atoms,
$R_{15}$ represents an alkyl lithium having 1 to 20 carbon atoms, an alkyl sodium having 1 to 20 carbon atoms, an alkyl potassium having 1 to 20 carbon atoms, an alkyl magnesium bromide having 1 to 6 carbon atoms or an alkyl magnesium chloride having 1 to 6 carbon atoms,
$X_1$, $X_2$, $X_3$, $X_4$ and $X_5$ independently represent nitrogen or carbon, provided that at least one is nitrogen, and
a is an integer of 0 to 20.

Advantageous Effects

According to the present invention, by preparing an anionic polymerization initiator using a continuous reactor, it is possible to prevent instability and inactivation of the polymerization initiator and deterioration of the physical properties of the SSBR, to minimize the by-products and unreacted products, and to epochally improve the conversion rate of the polymerization initiator.

In addition, in the present invention, the polymerization initiator may be synthesized by a continuous polymerization reaction and then introduced into a polymerization tank simultaneously with raw materials of SSBR to prepare the SSBR, whereby problems such as deterioration of physical properties of the SSBR can be minimized, as well as the production of products having stable and constant quality can be allowed.

Furthermore, since the method for preparing an anionic polymerization initiator of the present invention has a higher yield while having a shorter reaction time over the batch-wise reactor, it is possible to exhibit excellent effects, such as being capable of reducing the preparation process time economically.

Also, due to high yield, economic efficiency and stable quality for mass production can be secured, as well as manufacturing process time can be significantly reduced.

BRIEF DESCRIPTION OF DRAWINGS

FIG. 1 is a schematic configuration diagram of a device for manufacturing an anionic polymerization initiator according to one embodiment of the present invention.

FIG. 2 is a schematic configuration diagram of a device for manufacturing an anionic polymerization initiator according to another embodiment of the present invention.

FIG. 3 shows the detailed structure of microchannels and the fluid flows in the microchannels, according to another embodiment of the present invention.

FIG. 4 shows a separated configuration and a combined configuration of a lower microchannel and an upper microchannel, according to another embodiment of the present invention.

FIG. 5 is a schematic configuration diagram of a device for manufacturing an anionic polymerization initiator according to another embodiment of the present invention.

BEST MODE

Hereinafter, the present invention will be described in detail. The following detailed description is intended to illustrate embodiments of the present invention in detail, and thus, even if there are definite expressions, the scope of the right defined from the claims is not limited.

If an anion polymerization initiator is prepared in a batch-wise reactor, which is a prior art, there have been problems that synthesis yield is low and an initiator inactivation reaction occurs due to storage, and the like.

Accordingly, the present inventors have found that the above-described problems can be solved through the manufacturing method according to the present invention, and the present invention has been accomplished.

The present invention provides a method for preparing an anionic polymerization initiator comprising a step of introducing at least one amine compound selected from compounds of Formulas 1 and 2 below and an organometallic compound into a continuous reactor and reacting them:

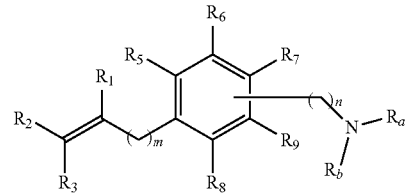

[Formula 1]

In Formula 1 above, $R_1$, $R_2$, $R_3$, $R_5$, $R_6$, $R_7$, $R_8$ and $R_9$ independently represent hydrogen or an alkyl group having 1 to 6 carbon atoms, $R_a$ and $R_b$ independently represent hydrogen or an alkyl group having 1 to 5 carbon atoms, and n and m are each an integer of 0 to 20;

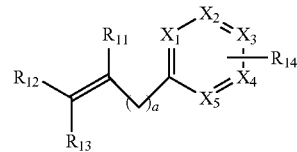

[Formula 2]

In Formula 2 above, $R_{11}$, $R_{12}$, $R_{13}$ and $R_{14}$ independently represent hydrogen, an alkyl group having 1 to 6 carbon atoms, an alkenyl group having 1 to 6 carbon atoms or an alkynyl group having 1 to 6 carbon atoms, $X_1$, $X_2$, $X_3$, $X_4$ and $X_5$ independently represent nitrogen or carbon, provided that at least one is nitrogen, and a is an integer of 0 to 20.

In the present invention, the term "alkyl group" is defined as a functional group derived from a linear or branched saturated hydrocarbon.

A specific example of the alkyl group may include a methyl group, an ethyl group, an n-propyl group, an iso-propyl group, an n-butyl group, a sec-butyl group, a tert-butyl group, an n-pentyl group, an 1,1-dimethylpropyl group, an 1,2-dimethylpropyl group, a 2,2-dimethylpropyl group, an 1-ethylpropyl group, a 2-ethylpropyl group, an n-hexyl group, an 1-methyl-2-ethylpropyl group, an 1-ethyl-2-methylpropyl group, an 1,1,2-trimethylpropyl group, an 1-propylpropyl group, an 1-methylbutyl group, a 2-methylbutyl group, an 1,1-dimethylbutyl group, an 1,2-dimethylbutyl group, a 2,2-dimethylbutyl group, an 1,3-dimethylbutyl group, a 2,3-dimethylbutyl group, a 2-ethylbutyl group, a 2-methylpentyl group and a 3-methylpentyl group, and the like.

In the present invention, "alkenyl group" or "alkynyl group" means that at least one carbon-carbon double bond or triple bond is contained in the middle or end of the alkyl group as defined above.

In addition, in the present invention, "heteroatom" means oxygen, sulfur, nitrogen, phosphorus, silicon, bromine, chlorine or iodine, and the like.

In one example, the compound of Formula 1 above may comprise a compound of Formula 3 below:

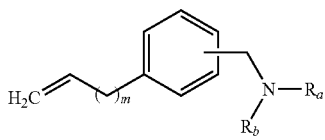

[Formula 3]

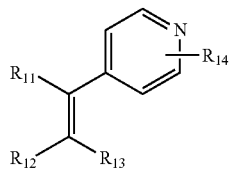

[Formula 8]

In Formula 3 above, $R_a$ and $R_b$ independently represent hydrogen or an alkyl group having 1 to 5 carbon atoms, and m is an integer of 0 to 20.

Specifically, the compound represented by Formula 3 used in the present invention may comprise Formula 6 below:

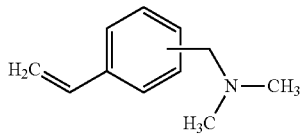

[Formula 6]

For example, the compound of Formula 6 above may be 2-vinyl-N,N-dimethylbenzylamine, 3-vinyl-N,N-dimethylbenzylamine or 4-vinyl-N,N-dimethylbenzylamine.

In one example, the compound of Formula 2 above may comprise a compound of Formula 4 or 5 below:

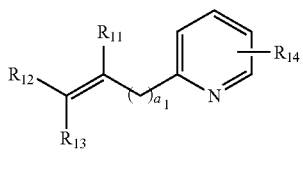

[Formula 4]

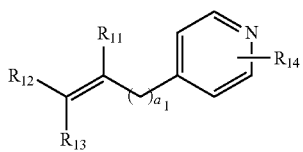

[Formula 5]

In Formulas 4 and 5 above, $R_{11}$, $R_{12}$, $R_{13}$ and $R_{14}$ each represent hydrogen, an alkyl group having 1 to 6 carbon atoms, an alkenyl group having 1 to 6 carbon atoms, or an alkynyl group having 1 to 6 carbon atoms, and $a_1$ is an integer of 0 to 10.

Specifically, the compound of Formula 4 above may comprise Formula 7 below, and the compound of Formula 5 above may comprise Formula 8 below:

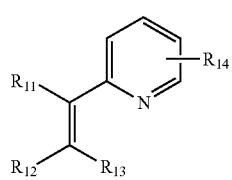

[Formula 7]

In Formula 7 or 8 above, $R_{11}$, $R_{12}$, $R_{13}$ and $R_{14}$ each represent hydrogen or an alkyl group having 1 to 6 carbon atoms, an alkenyl group having 1 to 6 carbon atoms, or an alkynyl group having 1 to 6 carbon atoms.

For example, the compound of Formula 7 and/or Formula 8 of the present invention may be 2-vinylpyridine or 4-vinylpyridine.

The organometallic compound may comprise an organic component and a metal component, and optionally, may further comprise a Br (bromine) element or a chlorine (Cl) element. Here, the organic component may be composed of an alkyl group having 1 to 10 carbon atoms, an aryl group, an alkenyl group, or the like. Specifically, the organic component may be an n-butyl group, an n-pentyl group, an s-butyl group or a t-butyl group, and more specifically, an n-butyl group. Furthermore, the metal component may be an alkali metal or an alkali earth metal. Specifically, it may be lithium, sodium, potassium, magnesium, rubidium, cesium, strontium, beryllium or calcium, and more specifically lithium.

For example, the organometallic compound may comprise at least one selected from the group consisting of an organic alkali metal compound and an organic alkali earth metal compound. Specifically, as the alkali metal compound, at least one selected from the group consisting of an alkyl lithium, an aryl lithium, an alkenyl lithium, an alkyl sodium, an aryl sodium, an alkenyl sodium, an alkyl potassium, an alkenyl potassium and an aryl potassium can be used, and more specifically, n-butyl lithium (NBL) can be used. In addition, the alkali earth metal compound may be an organomagnesium compound containing a Br (bromine) element or a chlorine (Cl) element, or may be an organocalcium compound or an organostrontium compound, and more specifically, the alkali earth metal compound having 1 to 6 carbon atoms, including methylmagnesium bromide ($CH_3MgBr$), ethylmagnesium bromide ($CH_3CH_2MgBr$), methylmagnesium chloride ($CH_3MgCl$), ethylmagnesium chloride ($CH_3CH_2MgCl$), and the like, can be used.

The compound of Formula 1 and/or Formula 2 above; and the organometallic compound, which each comprise a solvent, may be introduced into a reactor in the form of a solution of the compound of Formula 1 and/or Formula 2 above; and a solution of the organometallic compound.

As the solvent, a solvent, which does not react with an anion, as a hydrocarbon compound can be used, and specifically, at least one selected from linear hydrocarbon compounds such as pentane, hexane, heptane and octane; derivatives thereof having double branches; cyclic hydrocarbon compounds such as cyclohexane and cycloheptane; aromatic hydrocarbon compounds such as benzene, toluene and xylene; and linear and cyclic ethers such as dimethyl ether, diethyl ether, anisole and tetrahydrofuran can be used. Specifically, cyclohexane, hexane, tetrahydrofuran and diethyl ether, and more specifically, cyclohexane can be used.

The solution of the compound of Formula 1 and/or Formula 2 above may have a concentration of 0.1 to 50% by weight, and the solution of the organometallic compound may have a concentration of 0.1 to 30% by weight, and the balance may be the solvent.

The molar ratio of the compound of Formula 1 and/or Formula 2 above of the present invention; and the organometallic compound may be 1:5 to 5:1, specifically 1:1 to 1:1.2. If the molar ratio of the organometallic compound is higher or lower than the above range, there may be a problem that the generation of side reactants and unreacted products increases.

The solution of the compound of Formula 1 and/or Formula 2 above; and the solution of the organometallic compound may have a total flow rate of 0.01 to 500 g/min.

Specifically, when the solution of the compound of Formula 1 and/or Formula 2 above; and the solution of the organometallic compound are injected, the reaction temperature may be from −80 to 100° C., and the reaction time may be from 0.001 to 90 minutes. If the reaction temperature is too low, there may be a problem that the injected raw materials are frozen, and if the reaction temperature is too high, there may be a problem that the initiator is thermally decomposed. If the reaction time is too short, there may be a problem that the reaction conversion rate is low, and if the reaction time is too long, there may be a problem that the generation of side reactants increases.

Furthermore, a process of further mixing a polar additive may be included before injecting the compound of Formula 1 and/or Formula 2 above and the organometallic compound.

The polar additive may comprise at least one selected from tetrahydrofuran, ditetrahydrofuryl propane, diethyl ether, cycloalcohol ether, dipropyl ether, ethylene dimethyl ether, ethylene dimethyl ether, diethylene glycol, dimethyl ether, cycloamyl ether, dipropyl ether, ethylenedimethyl ether, ethylenedimethyl ether, diethylene glycol, dimethyl ether, tertiary butoxyethoxyethane bis(2-dimethylaminoethyl) ether, (dimethylaminoethyl) ethyl ether, dioxane, ethylene glycol dimethyl ether, ethylene glycol dibutyl ether, diethylene glycol dimethyl ether, diethylene glycol dibutyl ether, dimethoxybenzene, 2,2-bis(2-oxolanyl) propane, dipiperidinoethane, pyridine, quinuclidine, trimethylamine, triethylamine, tripropylamine, tetramethylethylenediamine, potassium-tert-butyrate, sodium-tert-butyrate, sodium amylate, and triphenylphosphine.

According to a specific embodiment, a specific example of the reaction step includes a step in which a solution comprising at least one selected from 2-vinyl-N,N-dimethylbenzylamine, 3-vinyl-N,N-dimethylbenzylamine, 4-vinyl-N,N-dimethylbenzylamine, 2-vinylpyridine and 4-vinylpyridine as an amine compound; and an NBL solution as an organometallic compound solution can be injected into a mixer in a continuous reactor.

In one example, the reaction of this step is the same as the following Reaction Schemes 1 and/or 2, and Reaction Schemes 1 and/or 2 are each a reaction scheme of a 3-vinyl-N,N-dimethylbenzylamine solution or a 2-vinylpyridine solution; and the NBL solution, wherein as the solvent, cyclohexane can be used:

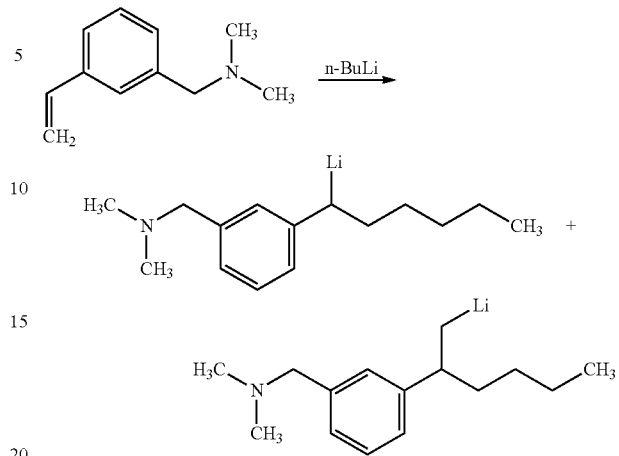

[Reaction Scheme 1]

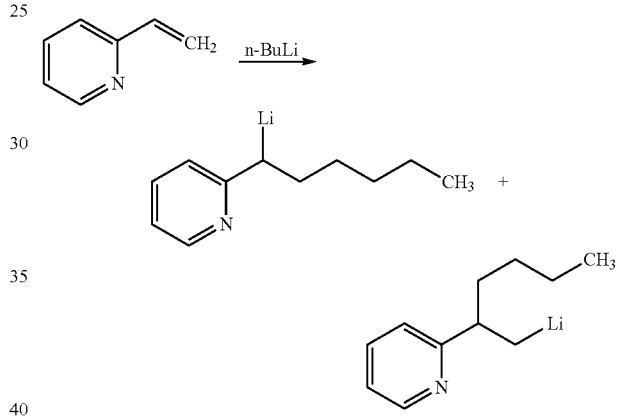

[Reaction Scheme 2]

In Reaction Scheme 1 above, the primary reactant may comprise the primarily reacted product and/or unreacted 3-vinyl-N,N-dimethylbenzylamine solution and the NBL solution, and in Reaction Scheme 2 above, the primary reactant may comprise the primarily reacted product and/or 2-vinylpyridine solution and the NBL solution.

If the compound of Formula 1 and/or Formula 2 above; and the organometallic compound (for example, NBL) are primarily reacted to have the molar ratio in the above-described range, the following amine compound-Li of the compound of Formula 1 or 2, which is a desired intermediate material, can be prepared with lowering the generation of the unreacted products and by-products.

After the step of reacting the compound of Formula 1 and/or Formula 2 above of the anionic polymerization initiator according to the present invention; and the organometallic compound, a step of supplying a conjugated diene compound to the continuous reactor may be included.

As the conjugated diene compound, at least one from 1,3-butadiene (BD), isoprene (IP), 2,3-dimethyl-1,3-butadiene, 1,3-pentadiene, 3-methyl-1,3-pentadiene, 1,3-heptadiene and 1,3-hexadiene can be used, and specifically, 1,3-butadiene or isoprene can be used. The conjugated diene compound, which comprises a solvent, may be introduced into the reactor in the form of a solution of the conjugated diene compound. Any solvent may be used as long as it is ordinarily usable, and specifically, cyclohexane, hexane, tetrahydrofuran and diethyl ether, and the like can be used as the solvent, and more specifically, cyclohexane can be used.

The conjugated diene compound solution may have a concentration of 1 to 100% by weight, and the balance may be the solvent.

The molar ratio of the compound of Formula 1 and/or Formula 2 above; and the conjugated diene compound may be 1:1 to 1:100, specifically 1:2 to 1:10. If the molar ratio of the conjugated diene compound is higher than the above range, there may be a problem that the viscosity of the solution increases, and if the molar ratio of the compound of the Formula 1 and/or Formula 2 above is lower than the above range, there may be a problem that the compound without attaching any diene compound increases.

The total flow rate of the primary reactant and the conjugated diene compound solution may be from 5 to 500 g/min, and the total reaction time may be from 3 to 60 minutes.

Specifically, when the conjugated diene compound is injected, the reaction temperature may be 10 to 100° C., and the reaction time may be 1 to 60 minutes. If the reaction temperature is too low, there may be a problem that the reaction initiation rate is slow, and if the reaction temperature is too high, there may be a problem that the initiator is thermally decomposed. If the reaction time is too short, there may be a problem that the reaction time is insufficient, and if the reaction time is too long, there may be a problem that unnecessary process cost is incurred in the state where the reaction is completed.

According to a specific embodiment, a specific example of the step of injecting the conjugate diene includes a step in which the reactant of the compound of Formula 1 and/or Formula 2 and the organometallic compound discharged from a first mixer and the isoprene solution may be mixed in a second mixer and reacted. At this time, the solvent in the isoprene solution may be cyclohexane.

According to one specific embodiment of the present invention, the pressure inside the continuous reactor may be from 1 to 30 bar.

In the present invention, the fluids of the introduced raw materials are sequentially introduced into the first mixer and the second mixer, and the primary reaction and the secondary reaction are each successively carried out to prepare an anionic polymerization initiator. That is, since in the preparation method of the present invention the reactions are performed stably and sequentially, the by-products and unreacted products are not generated unlike the conventional processes. Besides, the anionic polymerization initiator can be produced with high yield. Therefore, according to one specific embodiment of the present invention, the conversion rate of the amine compound can be 95% or more.

Furthermore, when the anionic polymerization initiator is prepared by the preparation method of the present invention and then directly introduced into the solution-polymerized styrene-butadiene rubber (SSBR) synthesis by an on-demand manner synthesis, the amine group such as the compound of Formula 1 and/or Formula 2 can be introduced into the front-end of the SSBR by solving the conventional initiator storage stability problem and improving the anion initiator reactivity.

In addition, the present invention provides a device for manufacturing an anionic polymerization initiator characterized in that the device comprises:

a mixer; and
a first inflow line and a second inflow line connected to the mixer, and
the first inflow line supplies at least one amine compound selected from the compounds of Formulas 1 and 2 according to claim 1, and the second inflow line supplies an organometallic compound.

Specifically, the mixer may comprise a first mixer and a second mixer connected in series, and
comprise first and second inflow lines connected to the first mixer; and a third inflow line connected to the second mixer,
wherein the third inflow line may supply a conjugated diene compound.

More specifically, the mixer may have a structure in which the first mixer and the second mixer connected in series are repeated.

In one example, at least one of the first and second mixers may be a static mixer. Specifically, the first mixer may be a first static mixer, and the second mixer may be a second static mixer.

The static mixers may each independently comprise at least one selected from the group consisting of a plate mixer, a Kenics mixer, and a Sulzer mixer. In addition, the static mixers may be connected in series.

Specifically, a first inflow line may be provided at one end of the first static mixer, and a second inflow line may be provided in a horizontal or vertical direction with respect to the first inflow line. Also, a third inflow line may be connected to the second static mixer.

In addition, the manufacturing device may further be equipped with a pressure control means for controlling an internal pressure. The amine compound of Formula 1 and/or Formula 2, the organolithium compound and the conjugated diene compound injected into the manufacturing device can be mixed and reacted while flowing in the same direction by the pressure control means.

In one example, at least one of the first and second mixers is a microreactor, wherein the microreactor may comprise a plurality of microchannels repeating branching and combining.

Specifically, the first mixer may be a first microreactor, and the second mixer may be a second microreactor.

In one example, any one of the first and second mixers may be a static mixer and the other may be a microreactor. Specifically, the first mixer may be a static mixer and the second mixer may be a microreactor. Or the first mixer may be a microreactor and the second mixer may be a static mixer.

In one example, at least one of the first and second mixers may be a structure in which a static mixer and a microreactor are sequentially connected. Specifically, the first mixer may comprise a first static mixer and a first microreactor, and the second mixer may comprise a second static mixer and a second microreactor. More specifically, the microreactor may be connected to the front end of the static mixer.

FIG. 1 is a schematic configuration diagram of a device for manufacturing an anionic polymerization initiator according to one embodiment of the present invention, wherein this device may comprise a primary reaction zone (1), a first static mixer (2), a first inflow line (3), a connecting tube (5), a secondary reaction zone (6), a second static mixer (7), a third inflow line (8), and an outlet (9).

FIG. 2 is a schematic configuration diagram of a device for manufacturing an anionic polymerization initiator according to another embodiment of the present invention, wherein the device according to this embodiment may comprise may be largely composed of a primary reaction zone (10) and a secondary reaction zone (20). The primary reaction zone (10) may comprise a first microreactor (11) and the secondary reaction zone (20) may comprise a second microreactor (21).

The first microreactor (11) is one type of continuous reactor, which may be equipped with a first inflow line (12), a second inflow line (13) and a plurality of microchannels (14, 15). For example, an amine compound of Formula 1 and/or Formula 2 may be injected into the first inflow line (12), and for example, an organometallic compound may be injected into the second inflow line (13).

The microchannels (14, 15) may be connected to or comprise the first inflow line (12) and the second inflow line (13). At least two microchannels (14, 15) may be provided, and they may form a plurality of branch points (meeting points) (16) by repeating branching and combining. Only two microchannels, that is, an upper microchannel (14) and a lower microchannel (15) are illustrated in the drawing, but three or more microchannels are also possible.

In the drawing, a plurality of microchannels (14, 15) forms a regular pattern by periodically branching while forming a rhombic shape, but the overall shape and branch pattern of the plurality of microchannels (14, 15) are not particularly limited, and if necessary, may be changed, and for example, may be a circle, an ellipse, a spiral, a polygon, and the like, and may also have mixed linear sections and curved sections or irregular patterns.

The number of repetitions of branching and combining in the microchannels (14, 15) is not particularly limited and may be, for example, 5 to 1000 times, preferably 10 to 500 times, more preferably 50 to 200 times. If the number of repetitions of branching and combining in the microchannels (14, 15), that is, the number of the branch points (meeting points) (16) is too small, the mixing effect may deteriorate, and if too large, the manufacturing may become difficult and the size of the mixer may become large.

The size of the microchannels (14, 15) is not particularly limited, and may be, for example, 10 to 10000 micrometers, preferably 50 to 5000 micrometers, and more preferably 100 to 2000 micrometers. Here, the size of the microchannels (14, 15) may mean a diameter, when the microchannels (14, 15) are circular, and an average diameter, when the microchannels (14, 15) are not circular. The diameter of the microchannels (14, 15) may be the same or different for each channel.

The first microreactor (11) can be divided and manufactured, and for example, completed by manufacturing an upper plate and a lower plate separately and then bonding two plates. The first inflow line (12), the second inflow line (13) and the microchannels (14, 15) may all be configured to be disposed on the same plane and at least one of the first inflow line (12), the second inflow line (13) and the microchannels (14, 15) may also be configured to be disposed on the different plane. In addition, the plurality of microchannels (14, 15) may be disposed in a two-dimensional (planar) shape, or may also have a three-dimensional arrangement structure such as a spiral. Furthermore, the plurality of microchannels (14, 15) is disposed in the horizontal direction, so that each channel may be located at the same height, or alternatively, it is disposed in the vertical direction, so that the height of each channel may be different.

For example, the fluid flows in a microchannel mixer manufactured from the divided upper and lower plates will be described as follows. The A solution (the organometallic compound) injected into the upper plate and the B solution injected into the lower plate (the amine compound of Formula 1 and/or Formula 2) may flow into the A solution at the upper part and the B solution at the lower part and branch, while passing through the first branch point. That is, the left side of the upper plate A solution and the left side of the lower plate B solution and the right side of the upper plate A solution and the right side of the lower plate B solution may be divided into the left flow channel and the right flow channel by the same amount, respectively. After branching the flow on the left side can be induced only to the upper plate, and the flow on the right side can be induced to flow only to the lower plate. Thereafter, the fluid flowing to the upper plate and the fluid flowing to the lower plate meet at the second branch point, where they can repeat the manner in which they branch again the same as described above and meet at the next point. Conceptually, the flow of two layers of A/B can be divided into A/B and A/B at a branch point and then combined up and down together to make them into four layers of A/B/A/B, and by repeating this, the flow is divided by the nth power of 2 and the interface between A and B is drastically increased, whereby the mixing effect can be maximized.

The second microreactor (21) can be connected with the first microreactor (11) in series via the connecting tube (17) and can be equipped with the third inflow line (22) and the outlet (26) and the plurality of microchannels (23) and a branch point (meeting point) (25). The primary reactant of the first microreactor (11) can be injected through the connecting tube (17), for example, the conjugated diene compound can be injected into the third inflow line (22) and the secondary reactant can be discharged into the outlet (26). The second microreactor (21) may be composed the same as or similar to the first microreactor (11).

FIG. 3 shows the detailed structure of microchannels and the fluid flows in the microchannels, according to another embodiment of the present invention, and FIG. 4 shows a separated configuration and a combined configuration of a lower microchannel and an upper microchannel, according to another embodiment of the present invention.

The first microreactor (11) may be composed including an upper plate and a lower plate. An upper microchannel (14) having an opened bottom may be formed on the upper plate and a lower microchannel (15) having an opened top may be formed on the lower plate, where the upper and lower microchannels (14, 15) may be combined to form a sealed flow channel in the longitudinal direction. The flow channel may have a rectangular cross section as in the drawing, and may also be manufactured into a circular shape, an elliptical shape, or other polygonal shapes. The upper and lower microchannels (14, 15) may have respective inflow lines (12a, 13a) and one common outlet (17a). The inflow lines (12a, 13a) may be connected to the inflow lines (12, 13) and the inflow lines (12a, 13a) themselves may also be extended outside the upper and lower plates to form the inflow lines (12, 13). The outlet (17a) may be connected to the connecting tube (17) and the outlet (17a) itself may also be extended outside the upper and lower plates to form the connecting tube (17).

The upper microchannel (14) may be equipped with a plurality of branch points (16a, 16b) disposed along the center and branch into two branches of the left and right branch channels (14a, 14b) at each branch point (16a, 16b), provided that each right branch channel (14b) may be extended and closed, and each left branch channel (14a) may be extended to the next branch point (16b) while being deflected toward the center.

Thus, the reason why one side of the branch channels is closed and the other side is continuously connected is to induce the fluid flow of the multi-layer structure. If one side of the branch channels is not closed, the two fluids may hardly be mixed or the mixing effect may be insignificant.

Similarly, the lower microchannel (15) may be equipped with a plurality of branch points (16a, 16b) disposed along the center and branch into two branches of the left and right branch channels (15a, 15b) at each branch point (16a, 16b), provided that each left branch channel (15a) may be extended and closed, and each right branch channel (15b) may be extended to the next branch point (16b) while being deflected toward the center.

Referring to FIG. 3, a first solution selected from a solution of an amine compound of Formula 1 and/or Formula 2 and a solution of an organometallic compound may be introduced into the inflow line (12a) of the upper microchannel (14), and a second solution can be introduced into the inflow line (13a) of the lower microchannel (15).

Thereafter, while the upper and lower microchannels (14, 15) are combined, for example, in the case of the point A, the two layered flow of the first solution layer in the upper microchannel (14) and the second solution layer in the lower microchannel (15) flows.

When the first branch point (16a) is reached, for example, in the case of the point B, the flow rate may increase, while the channel width is enlarged.

Thereafter, while passing through the first branch point (16a), for example, in the case of the point C, the flow may branch into a two layered flow of the left branch channels (14a, 15a) and a two layered flow of the right branch channels (14b and 15b). Up to this point, it is possible to maintain a two layered flow at approximately the same flow rate as the point A in each channel.

Thereafter, while each branch channel (14b, 15a) passes through the closed point, for example, in the case of the point D, since the left branch channel (14a) of the upper microchannel (14) is extended and the left branch channel (15a) of the lower microchannel (15) is closed, the left two layered flow flows only into the left branch channel (14a) of the upper microchannel (14). On the contrary, since the right branch channel (14b) of the upper microchannel (14) is closed and the right branch channel (15b) of the lower microchannel (15) is extended, the right two layered flow flows only into the right branch channel (15b) of the lower microchannel (15). At this time, since the fluid flows only into one side microchannel, the flow rate of each channel at the point D is reduced to about half of that at the point C.

Thereafter, at the second branch point (16b), for example, in the case of the point E, the left two layered flow which has flowed only upwards and the right two layered flow which has flowed only downwards may meet at the center to form a four layered flow (first solution layer/second solution layer/first solution layer/second solution layer).

According to repetitions of the above-described process, a multi layered flow can be then formed by the nth power of 2 at each branch point.

In short, after the blue liquid of the lower plate and the red liquid of the upper plate flow and are divided into left and right at a branch point, the right flow may flow only into the lower plate to be led to the center and the left flow may flow only into the upper plate to be led to the center. That is, the flows that have been introduced by being divided into upper and lower parts are divided into left and right, then are led to the center and gathered up and down again, so that according to repetitions of branch points, like that the two divided flows are combined at the center to become a four layered flow and the four divided flows are divided again into two at the next branch point and combined at the center to become a eight layered flow, the result is that the flow is divided into nth power of 2.

Thus, when the fluid flow in the microchannel branches right and left, two branched flows can be led to the center and combined up and down, and when the flow of fluid in the microchannel branches up and down, two branched flows can be combined left and right.

FIG. 5 is a schematic configuration diagram of a device for manufacturing an anionic polymerization initiator according to another embodiment of the present invention, which is an embodiment that static mixers (19, 28) are added to the device of FIG. 2. The static mixers (19, 28) may be connected with one or more mixers selected from the group consisting of a plate mixer, a Kenics mixer and a Sulzer mixer in series.

In FIG. 5, the primary reaction zone (10) may comprise the first microreactor (11) and the first static mixer (19), and the secondary reaction zone (20) may comprise the second microreactor (21) and the second static mixer (28). The microreactors (11, 21) and the static mixers (19, 28) may be each connected in series via the connecting tubes (17, 18, 27).

Besides, the manufacturing device according to the present invention may further be equipped with a pressure control means for controlling the pressure inside a continuous reactor, in order that each material injected into the continuous reactor may flow in parallel into the first microreactor (11) and the second microreactor (21) in the case of FIG. 2 and into the first microreactor (11), the first static mixer (19), the second microreactor (21) and the second static mixer (28) in the case of FIG. 5, and to prevent the flow in the reverse direction.

That is, according to another embodiment of the present invention, the continuous process type reactor may further be equipped with a pressure control means for controlling the internal pressure. The amine compound, the organometallic compound and the conjugated diene compound injected into the manufacturing device can be mixed and reacted while flowing in the same direction (downstream direction) at a pressure equal to or higher than normal pressure by the pressure control means.

The first inflow line according to the present invention may further supply an amine compound of Formula 1 and/or Formula 2; and at least one polar additive selected from tetrahydrofuran, ditetrahydrofuryl propane, diethyl ether, cycloamyl ether, dipropyl ether, ethylene dimethyl ether, ethylene dimethyl ether, diethylene glycol, dimethyl ether, tertiary butoxyethoxyethane bis(2-dimethylaminoethyl) ether, (dimethylaminoethyl) ethyl ether, dioxane, ethylene glycol dimethyl ether, ethylene glycol dibutyl ether, diethylene glycol dimethyl ether, diethylene glycol dibutyl ether, dimethoxybenzene, 2,2-bis(2-oxolanyl) propane, dipiperidinoethane, pyridine, quinuclidine, trimethylamine, triethylamine, tripropylamine, tetramethylethylenediamine, potassium-tert-butyrate, sodium-tert-butyrate, sodium amylate and triphenylphosphine in a mixture thereof.

In the device for manufacturing an anionic polymerization initiator according to the present invention, the reaction temperature of the first mixer may be −80 to 100° C. and the reaction time may be 0.001 to 90 minutes, and the reaction temperature of the second mixer may be 10 to 70° C. and the reaction time may be 1 to 60 minutes.

In addition, in the device for manufacturing an anionic polymerization initiator according to the present invention, the molar ratio of the amine compound of Formula 1 and/or Formula 2 injected into the first inflow line and the organometallic compound injected into the second inflow line may be 5:1 to 1:5, and the molar ratio of the amine compound of Formula 1 and/or Formula 2 injected into the first inflow line and the conjugated diene compound injected into the third inflow line may be 1:1 to 1:100.

Furthermore, the present invention provides an anionic polymerization initiator selected from compounds of Formulas 9 and 10 below:

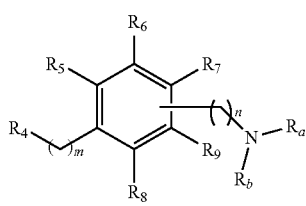

[Formula 9]

In Formula 9 above, $R_4$ represents an alkyl lithium having 1 to 20 carbon atoms, an alkyl sodium having 1 to 20 carbon atoms, an alkyl potassium having 1 to 20 carbon atoms, an alkyl magnesium bromide having 1 to 6 carbon atoms or an alkyl magnesium chloride having 1 to 6 carbon atoms, $R_5$, $R_6$, $R_7$, $R_8$ and $R_9$ each represent hydrogen or an alkyl group having 1 to 6 carbon atoms, $R_a$ and $R_b$ independently represent hydrogen or an alkyl group having 1 to 5 carbon atoms, and n and m are each an integer of 0 to 20;

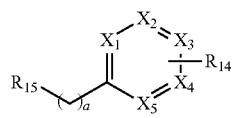

[Formula 10]

In Formula 10 above, $R_{14}$ represents hydrogen or an alkyl group having 1 to 6 carbon atoms, $R_{15}$ represents an alkyl lithium having 1 to 20 carbon atoms, an alkyl sodium having 1 to 20 carbon atoms, an alkyl potassium having 1 to 20 carbon atoms, an alkyl magnesium bromide having 1 to 6 carbon atoms or an alkyl magnesium chloride having 1 to 6 carbon atoms, $X_1$, $X_2$, $X_3$, $X_4$ and $X_5$ independently represent nitrogen or carbon, provided that at least one is nitrogen, and a is an integer of 0 to 20.

The anionic polymerization initiator of the present invention may have a long carbon chain on one of nitrogen by having the structures of Formulas 9 and 10 above.

In one example, the anionic polymerization initiator according to the present invention may comprise a compound of Formula 11 below:

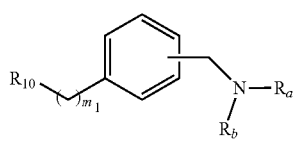

[Formula 11]

In Formula 11 above, $R_{10}$ represents an alkyl lithium having 1 to 20 carbon atoms, $R_a$ and $R_b$ independently represent hydrogen or an alkyl group having 1 to 5 carbon atoms, and $m_1$ is an integer of 0 to 10.

Specifically, an anionic polymerization initiator formed by reacting two or more of the compound of Formula 11 above may be included.

More specifically, the anionic polymerization initiator may comprise Formula 12 and/or Formula 13 below.

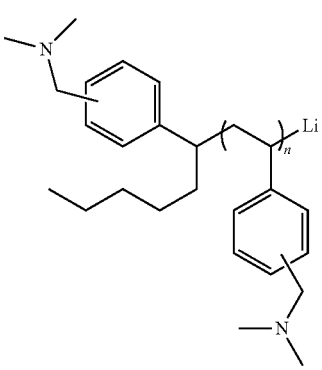

[Formula 12]

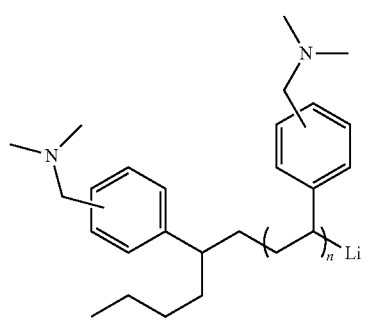

[Formula 13]

In one example, the anionic polymerization initiator according to the present invention may comprise a compound of Formula 14 or 15 below:

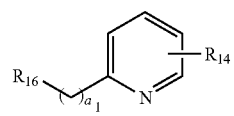

[Formula 14]

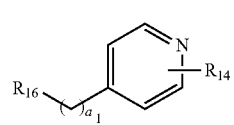

[Formula 15]

In Formulas 14 and 15 above, $R_{14}$ represents hydrogen or an alkyl group having 1 to 6 carbon atoms, $R_{16}$ represents an alkyl lithium having 1 to 20 carbon atoms, $a_1$ is an integer of 0 to 10.

Specifically, an anionic polymerization initiator formed by reacting two or more of the compound represented by Formula 14 or 15 above may be included.

More specifically, the anionic polymerization initiator may comprise Formulas 16, 17, 18 and/or 19 below.

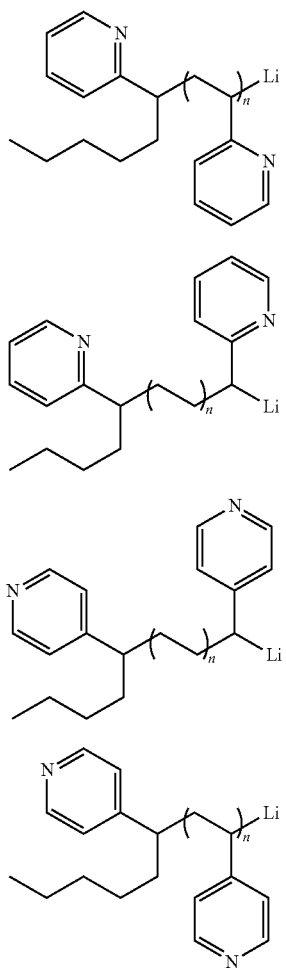

[Formula 16]

[Formula 17]

[Formula 18]

[Formula 19]

The anionic polymerization initiator can be prepared by using the above-described preparation method.

An anionic polymerization initiator prepared by using the above-described manufacturing device and preparation method is provided. The anionic polymerization initiator may be a lithium amide type in which one terminal is modified into an amine. That is, the anionic polymerization initiator provided in the present invention may be an anionic polymerization initiator containing a tertiary amine group, and may be a lithium amide-based anionic polymerization initiator whose one terminal is modified into an amine.

On the other hand, in the prior art, an anionic polymerization initiator was prepared by a batch-wise process and then used to prepare a solution-polymerized SSBR, or the preparation of an anionic polymerization initiator and a solution-polymerized styrene-butadiene rubber in a batch-wise reactor was carried out simultaneously in one pot. In the case of the former, the storage step of the modification initiator is necessarily required, and thus inactivation of the synthesized initiator is caused over time. This may adversely affect the post-processes to be a factor for lowering the physical properties of the finally synthesized SSBR, which makes it difficult to maintain a constant quality. In the case of the latter, it is a process of performing the polymerization reaction in the same batch-wise reactor simultaneously with the initiator synthesis reaction, whereby the problem of storage can be solved. However, it is difficult to confirm whether the modification initiator is properly synthesized, and the physical properties are also deteriorated more than the case of adding the synthesized initiator.

In the present invention, an anionic polymerization initiator is continuously prepared during transportation using a continuous reactor including at least one of a static mixer and a microreactor, whereby the side reaction can be prevented to obtain a high yield.

Furthermore, when the anionic polymerization initiator is prepared by the preparation method of the present invention and then directly introduced into the solution-polymerized styrene-butadiene rubber (SSBR) synthesis by an on-demand manner synthesis, the tertiary amine group can be introduced into the front-end of the SSBR by solving the conventional initiator storage stability problem and improving the anion initiator reactivity.

MODE FOR INVENTION

Hereinafter, the present invention will be described in more detail based on examples, but the following examples are for illustrating the present invention, and the scope of right of the present invention is not limited to the following examples.

Example 1

Three vacuum-dried stainless steel pressure vessels were prepared. 47 g of hexane, 100 g of 3-vinyl-N,N-dimethylbenzylamine and 101 g of tetramethylethylenediamine were placed in the first pressure vessel to prepare a 3-vinyl-N,N-dimethylbenzylamine solution. Then, 171 g of 2.5M liquid n-butyllithium and 77 g of hexane were placed in another pressure vessel to prepare an n-butyllithium solution.

The pressure of each pressure vessel was maintained at 4 bar. Then, using a mass flow meter, the 3-vinyl-N,N-dimethylbenzylamine solution was injected into a first inflow line at 0.5 g/min and the n-butyllithium solution was injected into a second inflow line at 0.5 g/min, where each flow meets on a T-union or Y-shaped channel. At this time, the width of the tube or channel was ⅛ inch, the temperature was kept at −30° C., and the internal pressure was maintained at 2 bar using a back pressure regulator. After the two raw materials were mixed, the residence time was adjusted to be 5 minutes. Then, the molar ratio of n-butyllithium was 1.0 time and the molar ratio of tetramethylethylenediamine was 1.4 times based on the molar ratio of 3-vinyl-N, N-dimethylbenzylamine. Next, an isoprene solution was injected into a third inflow line at 15 g/min.

Example 2

The anionic polymerization initiator was prepared in the same manner as in Example 1, except that the mixed solution, in which isomers of 2-vinyl-N,N-dimethylbenzylamine, 3-vinyl-N,N-dimethylbenzylamine and 4-vinyl-dimethylbenzylamine were mixed, was used other than the 3-vinyl-N,N-dimethylbenzylamine solution.

Example 3

The anionic polymerization initiator was prepared in the same manner as in Example 1, except that a static mixer other than the tube reactor was used.

Example 4

Three vacuum-dried stainless steel pressure vessels were prepared. 1000 g of hexane, 82 g of 2-vinylpyridine and 911 g of tetramethylethylenediamine were placed in a first pressure vessel to prepare a 2-vinylpyridine solution. Then, 484 g of 2.5M liquid n-butyllithium and 981 g of cyclohexane were placed in another pressure vessel to prepare an n-butyllithium solution.

The pressure of each pressure vessel was maintained at 5 bar. Then, using a mass flow meter, the 2-vinylpyridine solution was injected into a first inflow line at 1.0 g/min and the n-butyllithium solution was injected into a second inflow line at 1.2 g/min, where each flow meets on a T-union or Y-shaped channel. At this time, the width of the tube or channel was ⅛ inch, the temperature was kept at −30° C., and the internal pressure was maintained at 3 bar using a back pressure regulator. After the two raw materials were mixed, the residence time was adjusted to be 5 minutes. Then, the molar ratio of n-butyllithium was 1.0 time based on the molar ratio of 2-vinylpyridine. Next, a butadiene solution was injected into a third inflow line at 15 g/min.

Example 5

The anionic polymerization initiator was prepared in the same manner as in Example 4, except that the mixed solution of isomers comprising 2-vinylpyridine and 4-vinylpyridine was used instead of 2-vinylpyridine.

Example 6

The anionic polymerization initiator was prepared in the same manner as in Example 4, except that a tube reactor and a static mixer were used in combination.

Experimental Example 1

Conversion rates of the amine compounds and the conjugated diene compounds in Examples 1 to 6 were analyzed by gas chromatography (GC) and calculated by the following Equation 1.

Conversion rate (%) of amine compound or conjugated diene compound=100×(initial concentration of amine compound or conjugated diene compound−concentration of amine compound or conjugated diene compound after reaction)/initial concentration of amine compound or conjugated diene compound   [Equation 1]

Consequently, the conversion rate of 3-vinyl-N,N-dimethylbenzylamine and the conversion rate of isoprene in the anionic polymerization initiator of Example 1 were 99% and 99%, respectively; the conversion rate of vinyl-N,N-dimethylbenzylamine isomers and the conversion rate of isoprene in the anionic polymerization initiator of Example 2 were also 99% and 99%, respectively; and the conversion rate of 3-vinyl-N,N-dimethylbenzylamine and the conversion rate of isoprene in the anionic polymerization initiator of Example 3 were also 98% and 99%, respectively.

In addition, the conversion rate of 2-vinylpyridine and the conversion rate of butadiene in the anionic polymerization initiator of Example 4 were 99% and 99%, respectively; the conversion rate of vinylpyridine isomers and the conversion rate of butadiene in the anionic polymerization initiator of Example 5 were also 99% and 99%, respectively; and the conversion rate of 2-vinylpyridine and the conversion rate of butadiene in the anionic polymerization initiator of Example 6 were also 98% and 99%, respectively.

INDUSTRIAL APPLICABILITY

Since the present invention has a higher yield while having a shorter reaction time over the batch-wise reactor, it is possible to exhibit excellent effects, such as being capable of reducing the preparation process time economically.

The invention claimed is:

1. A method for preparing an anionic polymerization initiator comprising a step of introducing at least one amine compound selected from compounds of Formulas 3 to 5 below and an organometallic compound into a continuous reactor and reacting them; and a step of supplying a conjugated diene compound to the continuous reactor after the step of reacting the at least one amine compound and the organometallic compound, wherein the organometallic compound comprises at least one selected from the group consisting of an organic alkali metal compound and an organic alkali earth metal compound, the conjugated diene compound is at least one selected from 1,3-butadiene, isoprene, 2,3-dimethyl-1,3-butadiene, 1,3-pentadiene, 3-methyl-1,3-pentadiene, 1,3-heptadiene and 1,3-hexadiene, and the anionic polymerization initiator is selected from compounds of Formulas 11, 14 and 15 below:

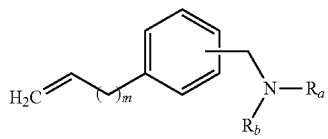

[Formula 3]

wherein, $R_a$ and $R_b$ independently represent hydrogen or an alkyl group having 1 to 5 carbon atoms, and m is an integer of 0 to 20,

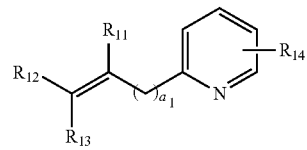

[Formula 4]

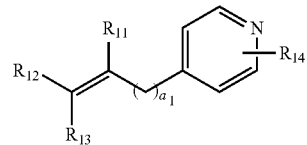

[Formula 5]

wherein, $R_{11}$, $R_{12}$, $R_{13}$ and $R_{14}$ each represent hydrogen, an alkyl group having 1 to 6 carbon atoms, an alkenyl group having 2 to 6 carbon atoms, or an alkynyl group having 2 to 6 carbon atoms, and $a_1$ is an integer of 0 to 10,

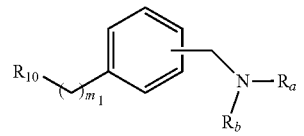

[Formula 11]

wherein, $R_{10}$ represents an alkyl lithium having 1 to 20 carbon atoms, $R_a$ and $R_b$ independently represent hydrogen or an alkyl group having 1 to 5 carbon atoms, and $m_1$ is an integer of 0 to 10,

[Formula 14]

[Formula 15]

wherein, $R_{14}$ represents hydrogen or an alkyl group having 1 to 6 carbon atoms, $R_{16}$ represents an alkyl lithium having 1 to 20 carbon atoms, $a_1$ is an integer of 0 to 10.

2. The method for preparing an anionic polymerization initiator according to claim 1, wherein the molar ratio of the at least one amine compound and the organometallic compound is from 5:1 to 1:5.

3. The method for preparing an anionic polymerization initiator according to claim 1, wherein the molar ratio of the at least one amine compound and the conjugated diene compound is from 1:1 to 1:100.

4. The method for preparing an anionic polymerization initiator according to claim 1, wherein the continuous reactor comprises:
a mixer; and
a first inflow line and a second inflow line connected to said mixer, and
the first inflow line supplies the at least one amine compound, and the second inflow line supplies the organometallic compound.

5. The method for preparing an anionic polymerization initiator according to claim 4,
wherein the mixer comprises a first mixer and a second mixer connected in series, and
comprises first and second inflow lines connected to the first mixer; and a third inflow line connected to the second mixer, and
the third inflow line supplies the conjugated diene compound.

6. The method for preparing an anionic polymerization initiator according to claim 5,
wherein at least one of the first and second mixers is a static mixer.

7. The method for preparing an anionic polymerization initiator according to claim 6,
wherein the static mixers are each independently at least one selected from the group consisting of a plate mixer, a Kenics mixer and a Sulzer mixer.

8. The method for preparing an anionic polymerization initiator according to claim 5,
wherein at least one of the first and second mixers is a microreactor, and
said microreactor comprises a plurality of microchannels repeating branching and combining.

9. The method for preparing an anionic polymerization initiator according to claim 5,
wherein at least one of the first and second mixers is a structure in which a static mixer and a microreactor are connected.

10. The method for preparing an anionic polymerization initiator according to claim 5,
wherein the reaction temperature of the first mixer is from −80° C. to 100° C. and the reaction time is from 0.001 to 90 minutes, and
the reaction temperature of the second mixer is from 10° C. to 100° C. and the reaction time is from 1 to 60 minutes.

* * * * *